United States Patent [19]

Maassarani

[11] Patent Number: 5,584,690
[45] Date of Patent: Dec. 17, 1996

[54] DENTAL CLEANING ASSEMBLY

[76] Inventor: Sami Maassarani, 1847 Lyster La., Troy, Mich. 48098

[21] Appl. No.: 541,274

[22] Filed: Oct. 12, 1995

[51] Int. Cl.$^6$ .............................. A61C 3/06; A61C 11/00
[52] U.S. Cl. ......................... 433/125; 433/116; 433/166
[58] Field of Search ................................. 433/125, 166, 433/116

[56] References Cited

U.S. PATENT DOCUMENTS

| | | |
|---|---|---|
| 1,516,933 | 11/1924 | Terranova . |
| 1,720,017 | 7/1929 | Touchstone ............................. 433/166 |
| 1,745,602 | 2/1930 | Chayes .................................... 433/166 |
| 1,834,726 | 12/1931 | Ozon . |
| 1,907,286 | 5/1933 | Chott ....................................... 433/166 |
| 2,300,828 | 11/1942 | Goldenberg ............................ 433/166 |
| 2,656,559 | 10/1953 | Wiseman .................................. 15/180 |
| 2,731,722 | 1/1956 | Wilen . |
| 2,789,352 | 4/1957 | Wiseman ................................ 433/166 |
| 3,126,021 | 3/1964 | May ........................................ 132/76.4 |
| 3,195,537 | 7/1965 | Blasi ....................................... 433/166 |
| 3,727,313 | 4/1973 | Graham ................................... 433/125 |
| 3,939,599 | 2/1976 | Henry et al. ............................ 433/125 |
| 4,424,036 | 1/1984 | Lokken ................................... 433/116 |
| 4,739,532 | 4/1988 | Behrend ................................. 433/166 |
| 4,869,277 | 9/1989 | Olsen ..................................... 433/166 |
| 5,131,846 | 7/1992 | Hall ........................................ 433/116 |

*Primary Examiner*—Gene Mancene
*Assistant Examiner*—Jinan Glasgow
*Attorney, Agent, or Firm*—Young & Basile, P.C.

[57] ABSTRACT

A dental cleaning assembly including a disposable dental tool including a main body tubular portion and a head portion disposed at right angles to the main body. A prophy cup is secured to a shaft projecting from the head portion so that the cup may be rotated to perform a tooth cleaning operation. A series of flexible bristles are secured to the head of the dental tool and extend forwardly therefrom in surrounding relation to the prophy cup so as to provide an anti-splatter shield for the cup to preclude splatter of toothpaste, saliva and blood. The bristles form an effective circumferential barrier around the prophy cup but yet allow complete freedom of movement of the prophy cup to perform the cleaning function and further allow potentially impacting paste to escape outwardly from the annular space between the prophy cup and the bristles to avoid impairment of the cleaning operation of the assembly.

16 Claims, 2 Drawing Sheets

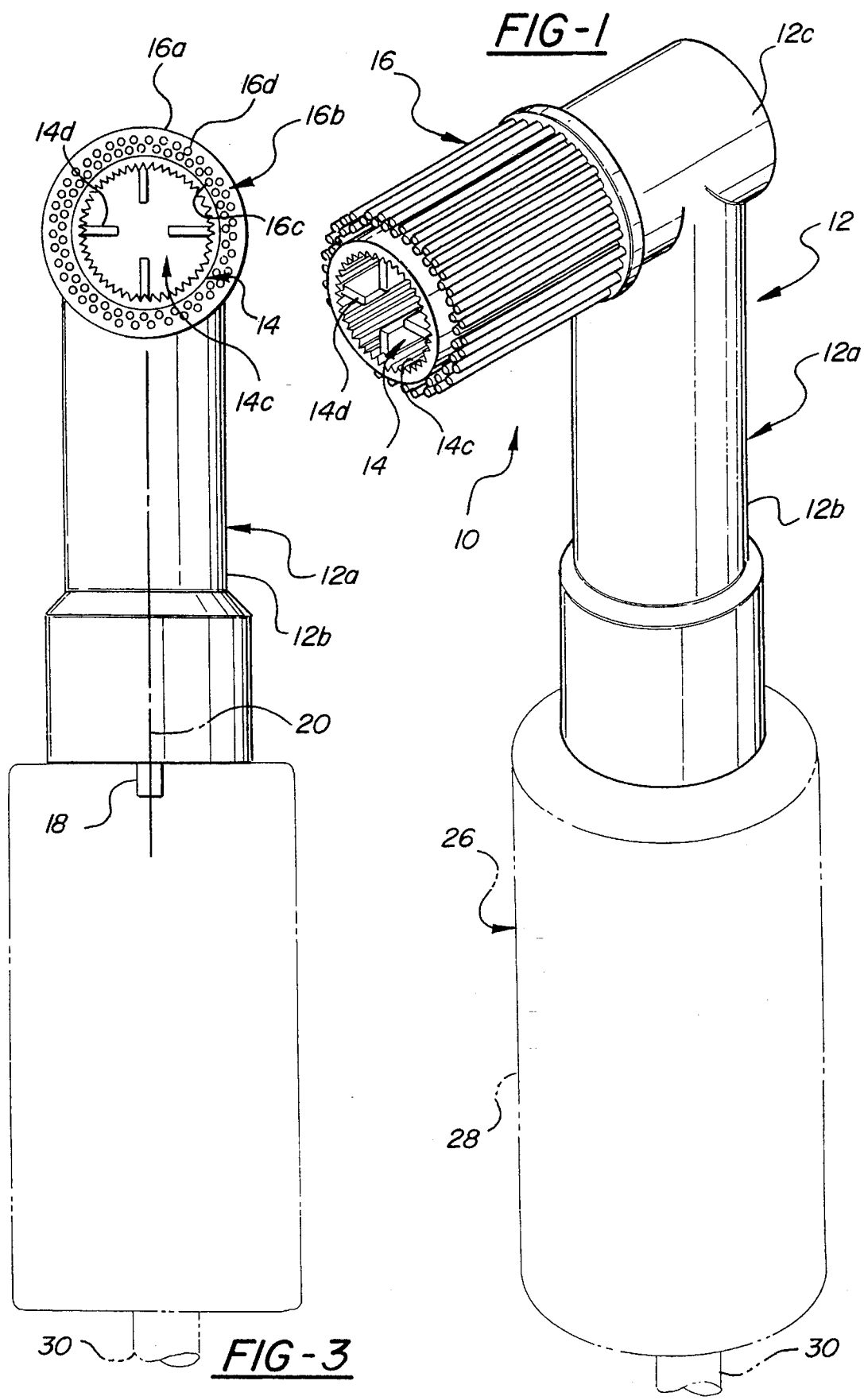

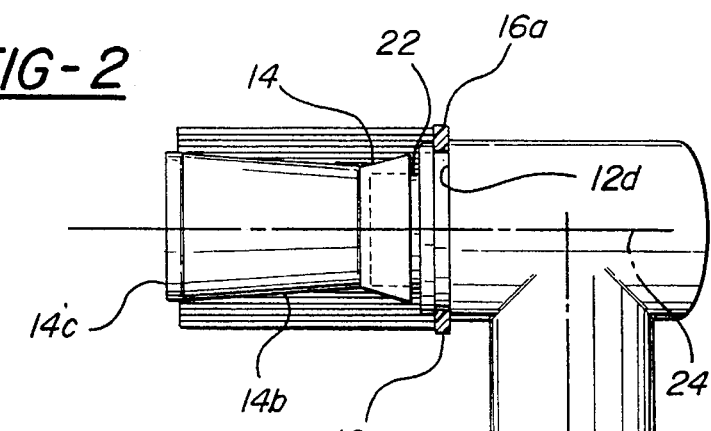
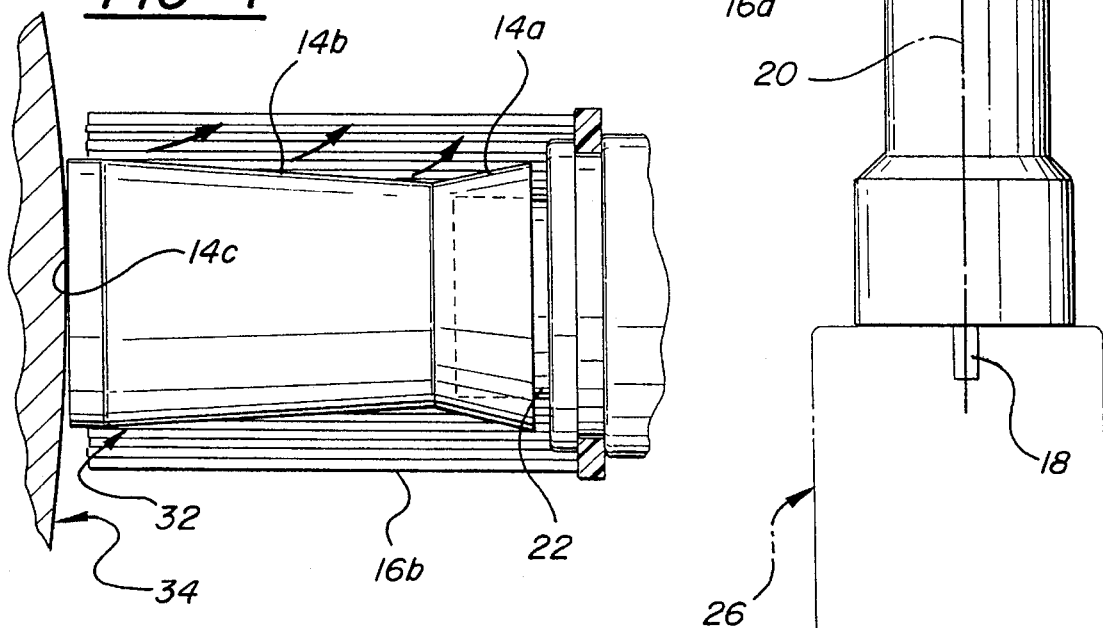
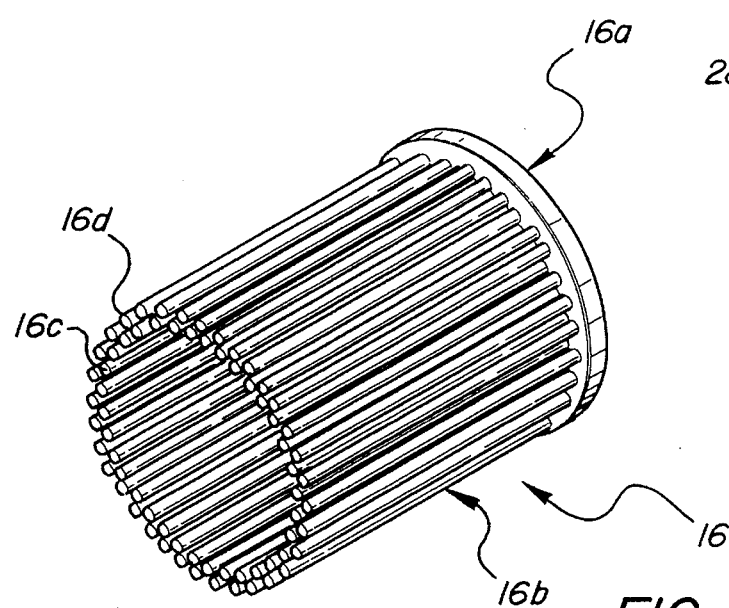

DENTAL CLEANING ASSEMBLY

BACKGROUND OF THE INVENTION

This invention relates to dental cleaning assemblies and more particularly to a dental tool for use in cleaning and polishing teeth.

Modern dental tooth cleaning procedures include the use of a power driven rotary flexible rubber cup which contains a quantity of slightly abrasive tooth cleaning paste.

The cleaning cup, more commonly called a prophy cup, may rotate at speeds of up to 5,000 rpm with the result that the cleaning paste is thrown off by the centrifugal force of the rotating cup. Not only can paste be thrown from the cup during the procedure but saliva and patient blood can likewise be splattered. With the increased concern in dentistry with respect to precluding the sharing of bodily fluids there is a need for an effective method of controlling and isolating this splatter of cleaning paste and patient body fluids. Several protective devices have been provided in the prior art which have purported to contain this splatter but these devices are either ineffective in containing the splatter and/or result in an impacting of the abrasive paste in a manner to impede the operation of the cleaning tool.

SUMMARY OF THE INVENTION

This invention is directed to the provision of an improved dental cleaning assembly.

More particularly, this invention is directed to the provision of a dental cleaning assembly including means for effectively containing splatter without interfering with the cleaning operation of the assembly.

The dental cleaning assembly of the invention includes a dental tool defining a head; a prophy cup mounted on the head; drive means on the head for rotating the cup; and a series of flexible bristles secured to the head and extending from the head in surrounding relation to the prophy cup. This arrangement provides an effective anti-splatter shield around the rotating cup and yet does not interfere with the effective cleaning operation of the assembly and avoids the prior art problem of impacting paste.

According to a further feature of the invention, the prophy cup includes a base portion positioned proximate the head and a cleaning portion defining a cleaning surface at the free forward end of the cleaning portion and the bristles extend forwardly from the head to a location proximate but spaced rearwardly from the cleaning surface. This specific arrangement provides adequate shielding for the centrifuging fluid and yet allows sufficient freedom of movement of the cleaning tip of the prophy cup so as to not interfere with the cleaning action of the prophy cup.

According to a further feature of the invention, the bristles are spaced radially outwardly from the prophy cup to define an annular space therebetween. This arrangement, again, allows the bristles to adequately shield the centrifuging fluid and yet does not interfere with the effective cleaning operation of the prophy cup.

According to a further feature of the invention, the bristles are arranged in a plurality of annular rows and the bristles in one annular row are circumferentially staggered with respect to the bristles in an adjacent annular row and coact with the bristles in adjacent annular rows to form a substantially complete circumferential barrier around the prophy cup. This arrangement allows the bristles to provide an effective shield for the spattering fluids and yet allows potentially impacting paste to leak between the bristles so as to avoid the impacting problem of the prior art.

BRIEF DESCRIPTION OF THE DRAWINGS

FIG. 1 is a prospective view of a dental cleaning assembly according to the invention;

FIG. 2 is a side view of the dental cleaning assembly;

FIG. 3 is a front view of the dental cleaning assembly;

FIG. 4 is a detail view of a portion of the dental cleaning assembly; and

FIG. 5 is a perspective view of a bristle assembly utilized in the dental cleaning assembly.

DETAILED DESCRIPTION OF THE PREFERRED EMBODIMENT

The invention dental cleaning assembly 10 includes a dental tool 12, a prophy cup 14, and a bristle assembly 16.

Dental tool 12 includes a body 12a formed of a suitable plastic material and including a main body tubular portion 12b and a tubular head portion 12c. A drive shaft 18 is suitably journaled in main body portion 12a for rotation about a central generally vertical axis 20 and a shaft 22 is journaled in and projects from the front end of head portion 12c and is rotable about an axis 24 arranged at substantially right angles with respect to axis 20. It will be understood that a transmission means (not shown) is provided at the intersection of axes 20 and 24 so that rotation of drive shaft 18 about axis 20 results in corresponding rotation of shaft 22 about axis 24.

Prophy cup 14 is formed of a suitable elastomeric material and includes a base portion 14a and a cleaning portion 14b defining a cleaning surface 14c at the free forward end of the prophy cup. Base portion 14a has a truncated conical configuration and cleaning portion 14b has a reverse truncated conical configuration. Cleaning portion 14b is generally tubular and therefore quite flexible and may, as shown, include a plurality of ribs 14d terminating at cleaning face 14c. Prophy cup 14 is mounted on shaft 22 for rotation about axis 24 by securing base portion 14a to the free end of shaft 22 so that rotation of drive shaft 18 results in corresponding rotation of the prophy cup about axis 24.

It will be understood that dental tool 12 is used in association with a hand piece 26 including an air motor 28 supplied by an air hose 30. The lower end of dental tool 12 is suitably removably secured to the upper end of handpiece 26 to establish a driving connection between air motor 28 and drive shaft 18 so that actuation of air motor 28 results in rotation of prophy cup 14. Dental cleaning assembly 10 is preferably disposable so that after use of the assembly to clean the teeth of a patient the cleaning assembly 10 is removed from the hand piece 26, suitably disposed of, and a new dental cleaning assembly 10 inserted into hand piece 26 for use on a new patient.

Bristle assembly 16 includes an annular base 16a and a plurality of bristles 16c extending forwardly from the annular base in an annular pattern. Annular base 16a is suitably secured to the front end of dental tool head portion 12c with bristles 16b extending forwardly from the head portion in concentric relation to axis 24 and in surrounding relation to prophy cup 14. Base portion 16a may be mechanically interlocked with the forward end of dental tool head portion 12c utilizing an annular groove 12d in the head portion or, preferably, may be fused to the head portion utilizing fusion welding, sonic welding or the like. For this purpose bristle assembly 16 is formed of a suitable plastic material that may be readily fused with the plastic material of dental tool 12. With bristle assembly base 16a suitably secured to head portion 12c and prophy cup 14 suitably secured to shaft 22, bristles 16b extend forwardly to a location proximate but spaced slightly rearwardly from the cleaning face 14c of the prophy cup. The bristles 16b are also spaced radially outwardly from the outer periphery of the prophy cup to define an annular space 32 therebetween.

Bristles 16b are preferably arranged in a pair of inner and outer annular concentric rows 16c and 16d with the bristles in row 16c circumferentially staggered with respect to the bristles in row 16d and with the bristles in the adjacent rows coacting to form a substantially complete circumferential barrier around the prophy cup. Bristles 16b preferably have a size, configuration, flexibility, and resiliency generally corresponding to the bristles of a typical toothbrush.

In operation, a quantity of somewhat abrasive paste is positioned in a hollow defined in the free forward end of the prophy cup and handpiece 26 is suitably manipulated to bring the cleaning face 14c of the prophy cup into proximity with the teeth 34 of a patient to provide a cleaning action on the surface 34a of the tooth. The cleaning action is accomplished by the rapidly rotating movement of the prophy cup about axis 24 in coaction with the abrasive action of the paste carried by the free end of the prophy cup. As the prophy cup spins rapidly, salvia from the patient's mouth as well as excess paste is thrown outwardly in a centrifugal action. This centrifuging material is intercepted by the splatter shield formed by the bristles 16b. However, the bristles 16b, by virtue of their flexibility, their radially outward spacing relative to the prophy cup, and their termination proximate but spaced rearwardly of the cleaning face 14c of the prophy cup, allow the cleaning tip of the prophy cup to move freely in all directions without interference from the bristles so as to optimize the cleaning action of the prophy cup. Whereas the annular spacing of the bristles from the prophy cup and the rearward disposition of the forward ends of the bristles from the cleaning face of the prophy cup allows substantial eccentric orbiting movement of the tip of the prophy cup relative to axis 24, even more significant excursions of the cleaning tip from a concentric position relation to axis 24 are made possible by the flexibility of the bristles which readily yield when contacted by the eccentrically orbiting cleaning tip of the prophy cup so as not to interfere with the scrubbing action of the prophy cup. The shielding anti-splatter action of the bristles is further improved by the utilization of inner and outer annular rows of bristles with the bristles in one row circumferentially staggered with respect to the bristles in an adjacent row and coacting with the bristles in the adjacent row to form a substantially complete circumferential barrier around the prophy cup. However, despite the substantially complete barrier formed by the coacting inner and outer rows, the bristles still yield readily to allow potentially impacting paste trapped in the annular space 32 between the prophy cup and the bristles to leak or ooze outwardly through the bristles so as to avoid any impairment to the operation of the dental tool caused by impacted paste in the space 32.

The invention dental cleaning assembly will be seen to effectively preclude splatter of cleaning paste and body fluids during a teeth cleaning procedure while allowing complete freedom of movement of the cleaning tip of the prophy cup to optimize the cleaning action and while allowing escape of potentially impacting paste to avoid impairment of the operation of the assembly as a result of impacted paste.

Whereas a preferred embodiment of the invention has been illustrated and described in detail it will be apparent that various changes may be made in the disclosed embodiment without departing from the scope or spirit of the invention.

I claim:

1. A dental cleaning assembly comprising:

a dental tool defining a head;

a cleaning and polishing prophy cup mounted on the head for rotation relative to the head about a central drive axis;

drive means on the head for rotating the cup relative to the head about the drive axis; and a series of flexible bristles fixedly secured to the head and extending forwardly from the head in surrounding relation to the prophy cup, whereby the prophy cup may be rotated about the drive axis to perform a dental cleaning operation while the bristles form a non-rotating flexible shield in surrounding relation to the rotating cup to minimize splattering and yet allow substantial eccentric orbiting movement of the rotating cup relative to the drive axis.

2. A dental cleaning assembly according to claim 1 wherein:

the tool includes a tubular main body portion defining a main body drive axis;

the head is tubular and defines the central drive axis; and the central drive axis is generally perpendicular to the main body drive axis.

3. A dental cleaning assembly according to claim 1 wherein:

the prophy cup defines a base portion positioned proximate the head and a cleaning portion defining a cleaning surface at a free forward end of the cleaning portion; and the bristles extend forwardly from the head to a location proximate but spaced rearwardly from the cleaning surface.

4. A dental cleaning assembly according to claim 1 wherein:

the bristles are spaced radially outwardly from the prophy cup to define an annular space therebetween.

5. A dental cleaning assembly according to claim 3 wherein:

the bristles are spaced radially outwardly from the prophy cup to define an annular space therebetween.

6. A dental cleaning assembly according to claim 1 wherein:

the bristles are arranged in a plurality of annular rows.

7. A dental cleaning assembly according to claim 6 wherein:

the bristles in one annular row are circumferentially staggered with respect to the bristles in an adjacent annular row and coact with the bristles in adjacent annular rows to form a substantially complete circumferential barrier around the prophy cup.

8. A dental cleaning assembly comprising:

a dental tool defining a head and including a drive shaft carried by the head for rotation about a drive axis and projecting forwardly relative to the head to define a free forward end;

a cleaning and polishing prophy cup formed of an elastomeric material and including a rearward base portion secured to the free forward end of the drive shaft so as to rotate the prophy cup relative to the head about the drive axis and a forward flexible tubular cleaning portion having a free forward end defining a cleaning surface; and a series of flexible bristles fixedly secured to the head and extending forwardly from the head in surrounding relation to the prophy cup whereby the prophy cup may be rotated about the drive axis to perform a dental cleaning operation while the bristles form a non-rotating flexible shield in surrounding relation to the rotating cup to minimize splattering and yet allow substantial eccentric orbiting movement of the rotating cup relative to the drive axis.

9. A dental cleaning assembly according to claim 8 wherein:

the tool includes a tubular main body portion defining a main body drive axis;

the head is tubular and defines a head drive axis generally perpendicular to the main body drive axis and coincident with the drive axis of the drive shaft.

10. A dental cleaning assembly according to claim 8 wherein:

the bristles extend forwardly to a location proximate but spaced rearwardly from the cleaning surface.

11. A dental cleaning assembly according to claim 8 wherein:

the bristles are spaced radially outwardly from the prophy cup to define an annular space therebetween.

12. A dental cleaning assembly according to claim 10 wherein:

the bristles are spaced radially outwardly from the prophy cup to define an annular space therebetween.

13. A dental cleaning assembly according to claim 8 wherein the bristles are arranged in a plurality of annular rows.

14. A dental cleaning assembly according to claim 13 wherein the bristles in one annular row are circumferentially staggered with respect to the bristles in an adjacent annular row and coact with the bristles in adjacent annular rows to form a substantially complete circumferential barrier around the prophy cup.

15. A dental cleaning assembly according to claim 8 wherein:

the bristles form a part of a bristle assembly including an annular base portion;

the bristles are secured to the annular base portion; and the annular base portion is fixedly secured to the head in surrounding relation to the head.

16. A dental cleaning assembly according to claim 15 wherein:

the tool is formed of a plastic material;

the bristle assembly is formed of a plastic material; and the base portion of the bristle assembly is fused to the head.

* * * * *